United States Patent [19]
Klaus

[11] Patent Number: 5,875,781
[45] Date of Patent: Mar. 2, 1999

[54] SHOULDER HARNESS FOR USE IN POSITIONING A PATIENT'S SHOULDERS WHILE LAYING ON A TABLE

[76] Inventor: Duane Klaus, 7 Rogers Wood, San Antonio, Tex. 78248

[21] Appl. No.: 15,742

[22] Filed: Jan. 29, 1998

[51] Int. Cl.⁶ .................................................. A61B 19/00
[52] U.S. Cl. ............................ 128/869; 128/875; 602/32
[58] Field of Search ................................ 128/846, 869, 128/870, 874, 875; 602/32–40

[56] References Cited

U.S. PATENT DOCUMENTS

| | | |
|---|---|---|
| 951,515 | 3/1910 | Solsem . |
| 1,320,032 | 10/1919 | Bailey .................................... 128/875 |
| 2,377,940 | 6/1945 | Hughes .................................... 602/39 |
| 2,450,298 | 9/1948 | Peterson et al. ........................ 128/875 |
| 3,046,982 | 7/1962 | Davis ...................................... 128/875 |
| 3,160,143 | 12/1964 | Gray . |
| 3,295,517 | 1/1967 | Stevens .................................... 602/19 |
| 4,010,744 | 3/1977 | Boyen ...................................... 602/32 |
| 4,303,041 | 12/1981 | Thompson ............................. 128/875 |
| 4,674,483 | 6/1987 | Frederick ................................. 602/40 |
| 5,370,605 | 12/1994 | Weed ....................................... 602/35 |
| 5,575,765 | 11/1996 | Foster ...................................... 602/32 |

Primary Examiner—Michael A. Brown
Attorney, Agent, or Firm—Miller, Sisson, Chapman & Nash, PC.

[57] ABSTRACT

A system for applying a force caudally to the shoulders of a patient laying flat on a hospital table for purposes of taking x-rays of the neck area of the patient. This system includes a shoulder harness having a band near the shoulders with straps attached to the band. The straps extend longitudinally across the body of the patient toward the feet and, at the edge of the table on which the patient is laying, the straps are directed downward by means of pulleys. Hanging on the ends of the straps are weights. If the straps are criss-crossed across the patient, they will tend to pull the patient's shoulders down and inward, allowing for a better x-ray view of the neck area of the patient.

9 Claims, 5 Drawing Sheets

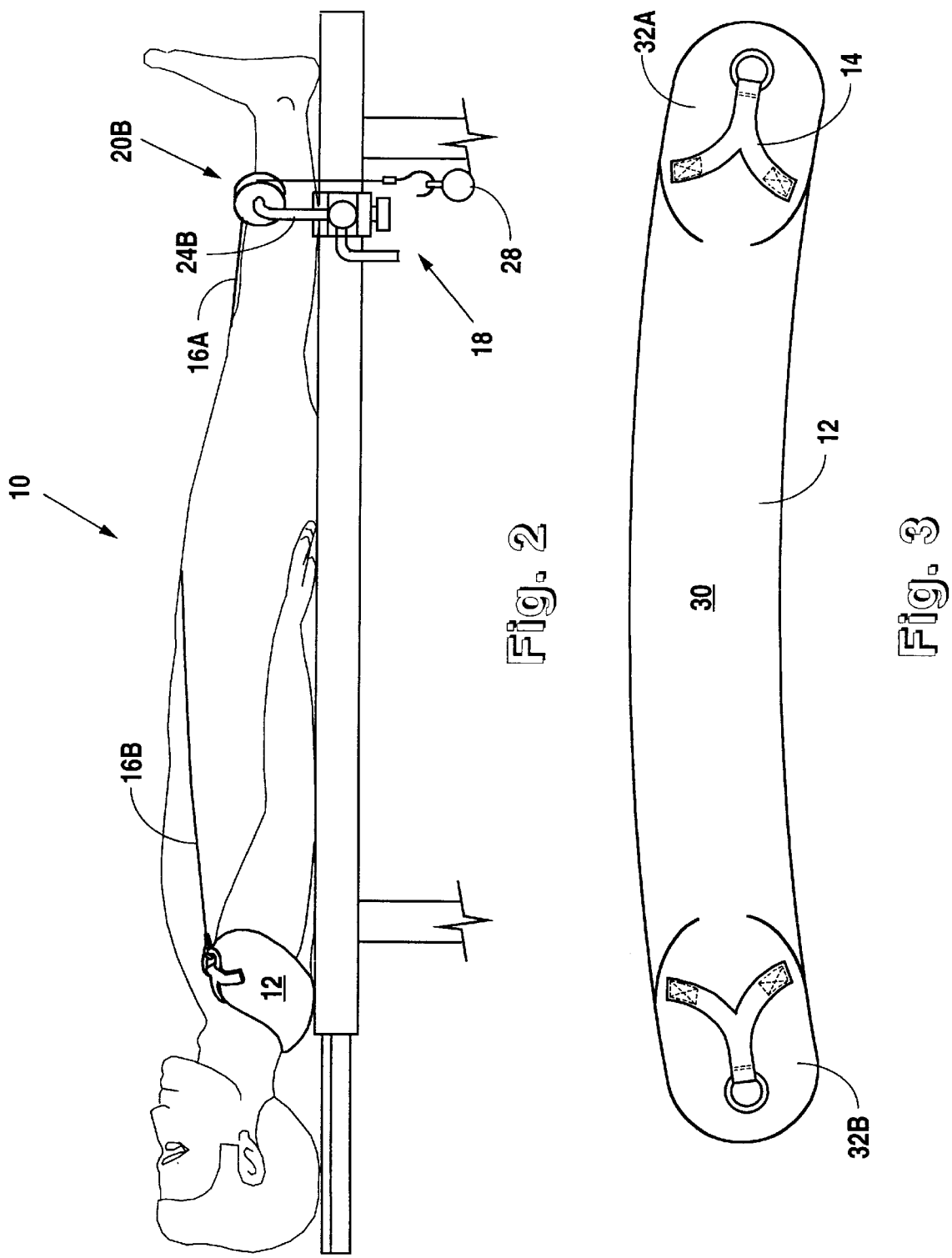

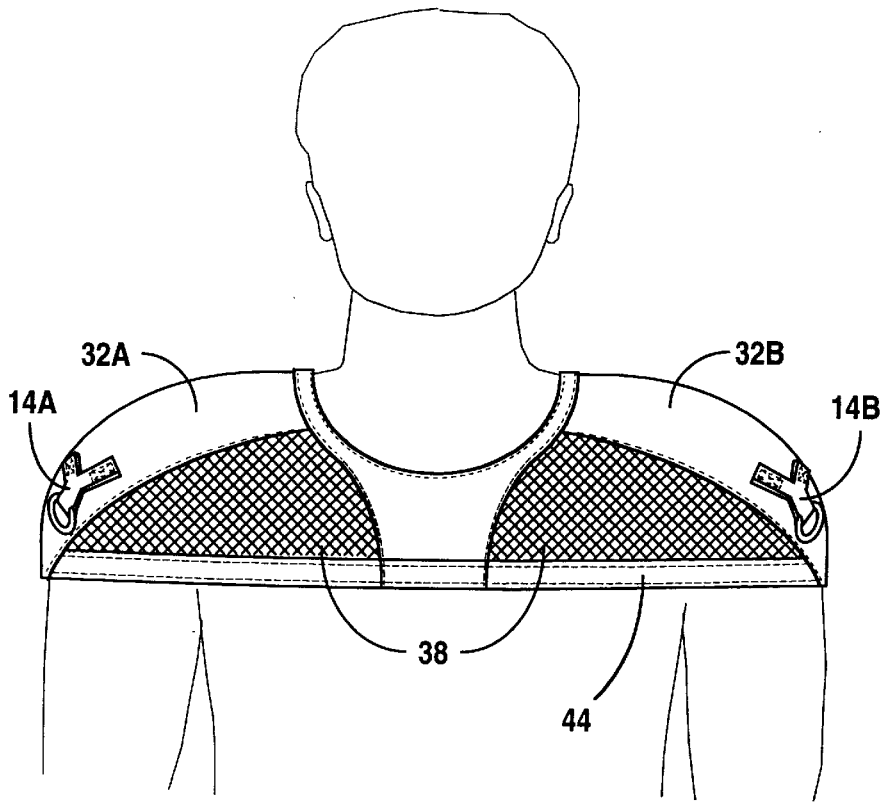
Fig. 4C
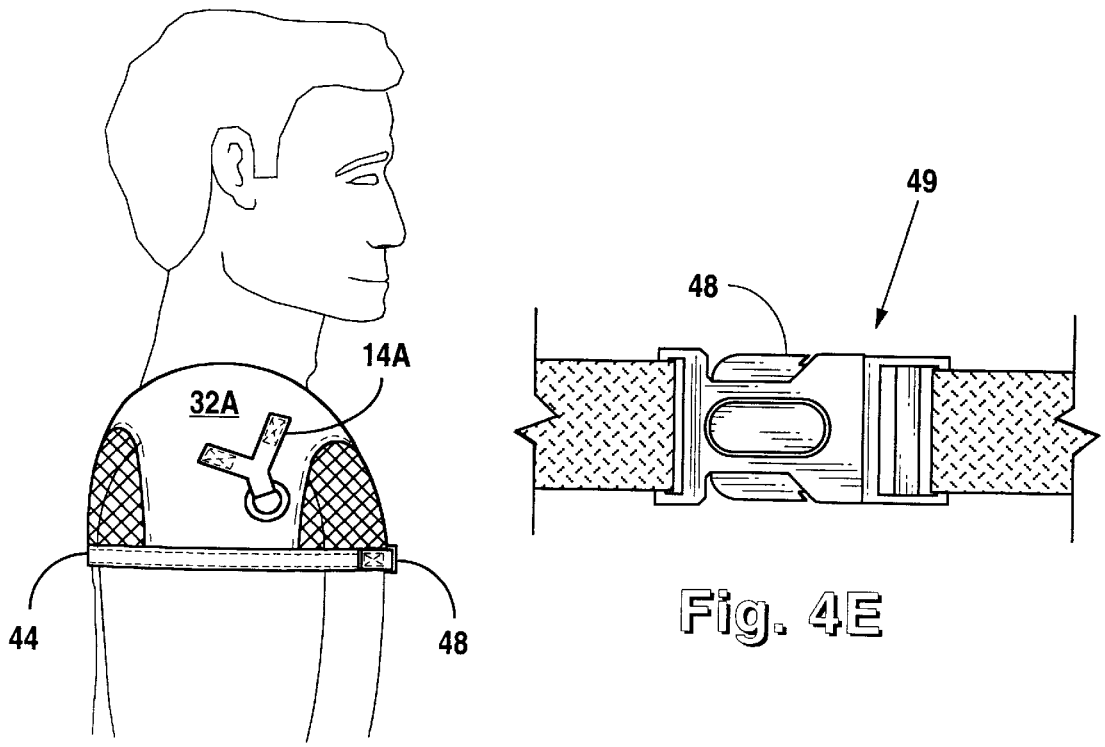
Fig. 4D
Fig. 4E

SHOULDER HARNESS FOR USE IN POSITIONING A PATIENT'S SHOULDERS WHILE LAYING ON A TABLE

FIELD OF THE INVENTION

A system for applying a force caudally to the shoulders of a patient laying flat on a hospital table for the purposes of taking X-rays of the neck area of the patient, more specifically, a system including a shoulder harness having a band near the shoulder with straps attached to the band, the straps to pull the shoulders downward toward the feet of the patient to allow the X-ray of the neck area without the interference from bones in the shoulder area.

BACKGROUND OF THE INVENTION

For X-rays to provide a clear view of the desired area, the patient and machine must be positioned correctly to avoid interference from other areas of the body. For example, during surgery in the neck region of a patient, X-rays are frequently taken during an operation to evaluate the status of the surgeon's work and the position of the bones. To get a proper view of the neck, the shoulders sometimes need to be pulled caudally (toward the feet) with the patient laying flat on an examination table. By applying a force on the shoulders toward the feet of the patient, an X-ray view taken transverse to the axis of the neck will not be subject to interference by the bones of the patient's shoulder.

To provide a proper X-ray view of the neck area, technicians presently use adhesive tape to tape the patient's shoulders directly to the examination table to maintain them caudally during the operation. However, this is clumsy at best; and the tape sometimes loosens. If that occurs, a surgeon will manually apply pressure to the shoulders to draw them caudally while the neck is exposed to X-rays. It can be appreciated that the surgeon or technician manually handling the patient's shoulders is exposed to the radiation of the X-ray machine. What is needed, therefore, is a system that will urge the patient's shoulders caudally while the patient is laying flat on the examination table without the inconvenience or disadvantages of the presently used tape method. This system should allow the surgeon or technician to leave the room during the X-raying procedure and also positively maintain the shoulders caudally to provide a proper view of the neck region.

OBJECTS OF THE INVENTION

It is an object of the present invention to provide for a system that will maintain force on a patient's shoulders when the patient is laying flat on an examination table.

It is a further object of the present invention to provide for a system which will apply force caudally to a patient's shoulder region while the patient is laying flat on an examination table.

It is an additional object of the present invention to provide for a system that will adjustably assert a force caudally to the shoulder area of a patient in an amount selected to urge and maintain the shoulders in a position to allow proper X-raying of the neck of a patient laying flat on an examination table.

It is another object of the present invention to provide for a simple, convenient system for location about the upper torso of a patient that will allow a force to be adjustably applied caudally to a patient laying flat on an examination table, such force for locating the shoulders of the patient in a position sufficient for a proper X-ray view of the neck to be taken.

It is yet another object of the present invention to provide for a system to properly locate the shoulders of a patient laying flat on an examination table so as to provide proper views of the neck of the patient, such device allowing the personnel to be absent from the area of the patient so as not to be exposed to X-ray radiation.

SUMMARY OF THE INVENTION

These and other objects are provided for in a system for applying a force caudally to the shoulders of a patient laying flat on an examination table, the system comprising a shoulder harness member to engage the shoulders of the patient and two straps for engaging the harness and urging the shoulders caudally.

These and other objects are provided in a system for applying a force caudally to the shoulders of a patient laying flat on an examination table, the system comprising a shoulder harness engaging the shoulders of the patient, further including a shoulder band laying adjacent to each shoulder of the patient, the band for attaching a strap to which means to apply tension is engaged to apply a force caudally.

These and other objects are provided for in a system including a shoulder harness with bands, the bands attached to straps to which is applied a tensional force to urge the shoulders of the patient caudally while the patient is laying flat on an examination table.

BRIEF DESCRIPTION OF THE DRAWINGS

FIG. 2 is a side elevational view of the system of Applicant's present invention as applied to a human patient laying on an examination table.

FIG. 3 is a top elevational view of the shoulder harness member of Applicant's present invention.

FIGS. 4A, 4B, 4C, and 4D are top, front, rear, and side elevational views, respectively, of a shoulder harness member of Applicant's present invention.

FIG. 4E is an illustration of an adjustable clasp.

DETAILED DESCRIPTION OF THE PREFERRED EMBODIMENT

Figures 1, 1A:
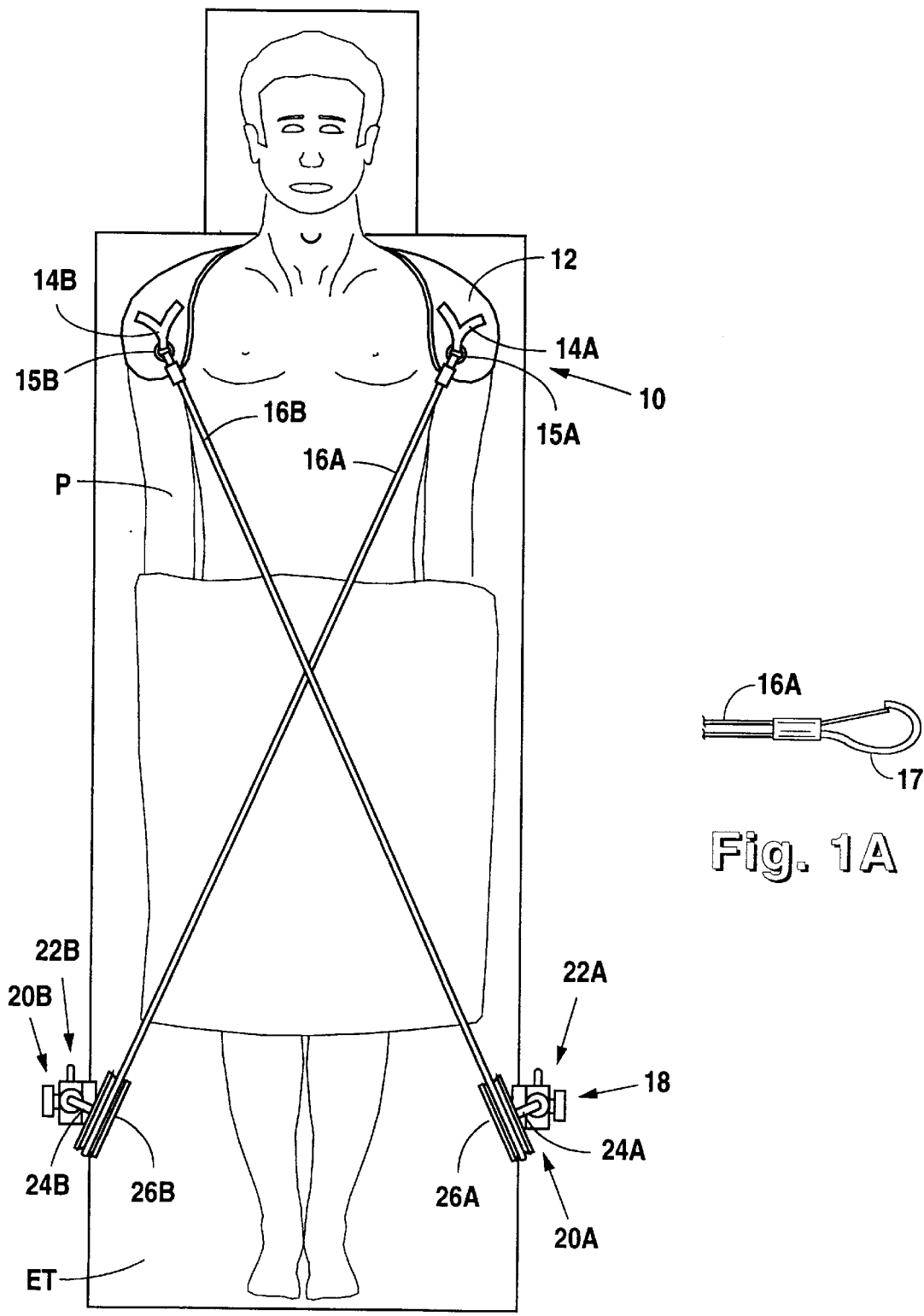
FIG. 1 is a top elevational view of a patient on an examination table featuring Applicant's system for urging and maintaining the shoulders of the patient caudally.
FIG. 1A is an elevational view of the clip which attaches the strap to the band.
Figure 4A:
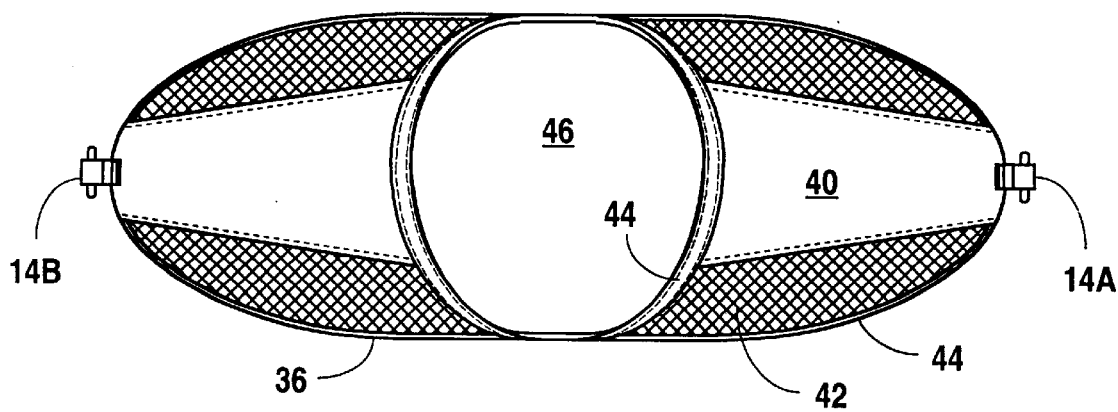
Figure 4B:
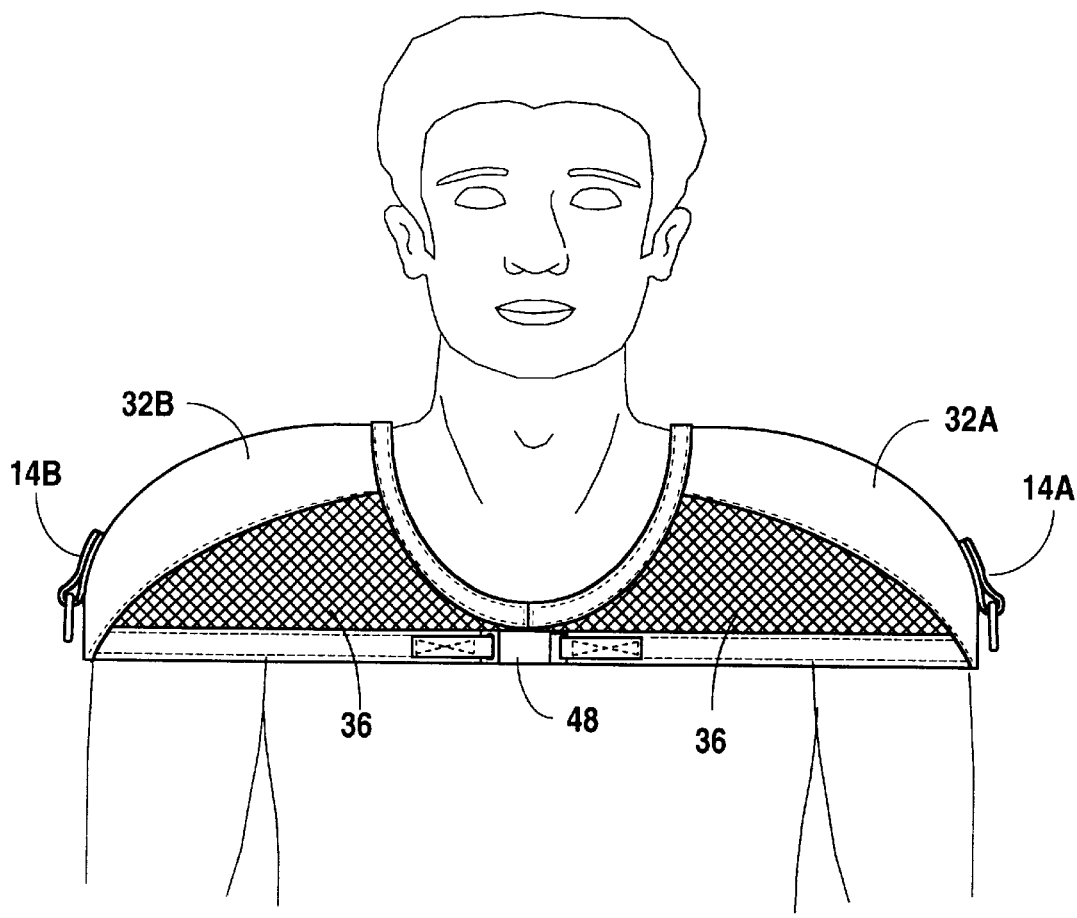

FIG. 1 illustrates the major components of Applicant's present invention. They are seen to be comprised of a shoulder harness member (12) assigned to lay adjacent a portion of patient's (P) upper torso, the portion of the upper torso engaged to include the shoulders and to further have attachment bands (14a) and (14b) attached to the shoulder harness member at or near the portions of the shoulder harness member that engage the patient's shoulders. Attached to the attachment bands (14a) and (14b) are rings (15a) and (15b), the rings typically metal or plastic to which are attached cables (16a) and (16b) through the use of metal or plastic clips (17) (see FIG. 1A). Thus, in the preferred embodiment illustrated in FIG. 1, the shoulder harness is seen to have a pair of attachment bands with a pair of rings and tensioning cables extending therefrom. The cables engage tensioning means (18), the tensioning means typically having two portions including a first portion (20a) which engages one edge of examination table (ET) and a second portion (20b) which engages the opposite edge of examination table (ET). First and second portions of tensioning means (18) function to apply tension in cables (16a) and (16b), which tension is transmitted to the patient to attachment bands (14a) and (14b) and shoulder harness (12) to urge the shoulders caudally (toward the patient's feet).

FIG. 2 illustrates in side elevational view the system of Applicant's present invention. It illustrates how tensioning means (18), more specifically second portion (20b) thereof, is constructed. Both the first portion (20a) and second portion (20b) of tensioning means (18) are typically identically constructed. This construction includes clamps (22a) and (22b) the clamps holding a vertical arm (24a) and (24b) to which is attached a pulley (26a) and (26b). Hanging from a removed end of the cables are weights (28) which are applied to create tension in the cables, which tension is transmitted to the shoulders of the patient through the use of shoulder harness member (12). Weights can vary to use more or less tension as necessary.

FIG. 3 illustrates details of Applicant's shoulder harness member (12). More specifically, FIG. 3 illustrates that shoulder harness member (12) has a body portion (30) and distal portions (32a) and (32b). The body of the shoulder harness member is designed to contact at least a portion of a patient's upper torso and the distal portions of the body are designed to lay adjacent a patient's shoulders. The body portion, including distal portions, may be made of a fabric including cloth or mesh or a combination of cloth and mesh fabrics. A typical cloth would be cotton.

FIGS. 4A, 4B, 4C, and 4D illustrate an alternate preferred embodiment of shoulder harness member (12) of Applicant's present invention. This alternate preferred embodiment engages both the upper back and upper chest area of a patient by means of a fabric front portion (36) and a fabric rear portion (38). As can be seen, the alternate preferred embodiment illustrated in FIGS. 4A, 4B, 4C, and 4D is made partially of cloth (40) and partially of mesh (42). Moreover, shoulder harness member (12) is seen to have reinforcement seams (44) at the border thereof. Indeed, reinforcement seams (44) may define a neck opening (46) in shoulder harness member (12). The alternate preferred embodiment illustrated may also have an engagement strap (48) to help place the harness on the patient which is adjustable in length to help fit patients of different sizes (see FIG. 4E). FIG. 4E shows an adjustable strap (48) which engages a tension-fighting engagement buckle/clasp (49) attached to the harness opposite strap (48).

Figure 5A:
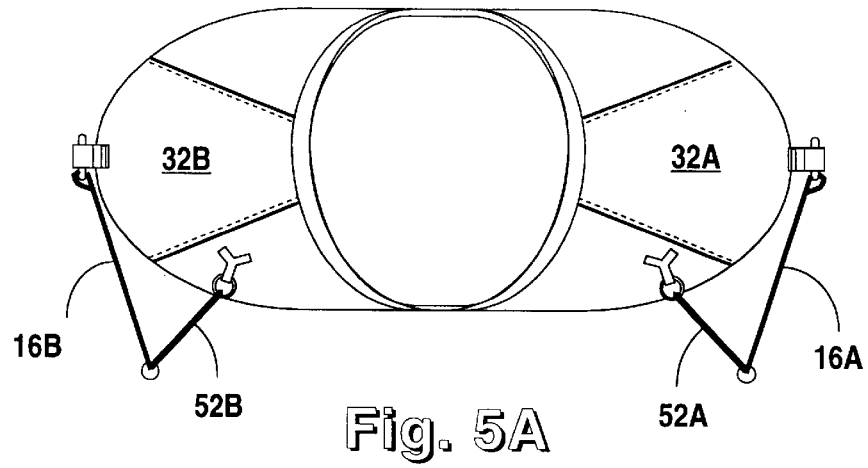
FIGS. 5A and 5B are top and front elevational views, respectively, of an alternate preferred embodiment of a shoulder harness member of Applicant's present invention.
Figure 5B:
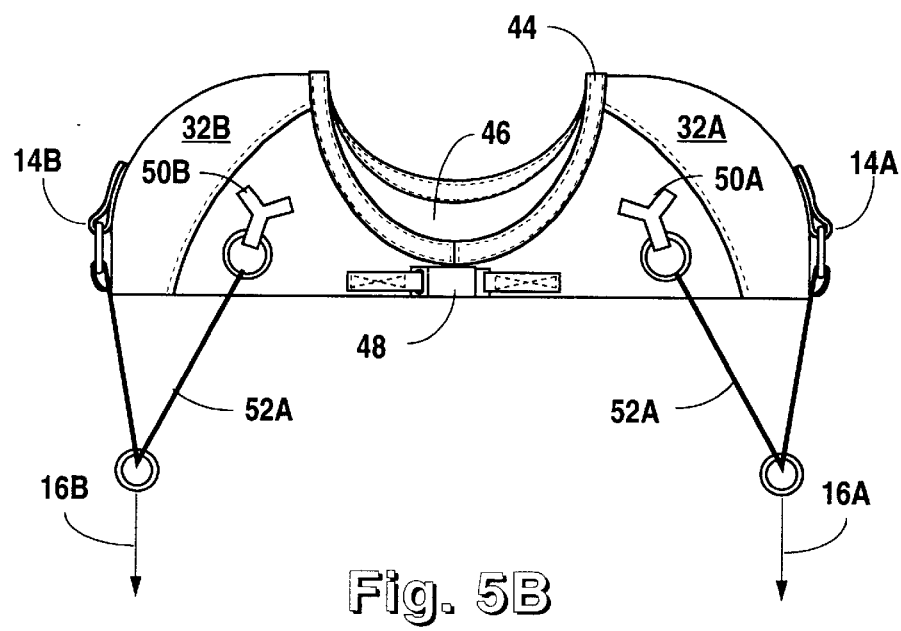

An additional alternate preferred embodiment of Applicant's shoulder harness member (12) is illustrated in FIGS. 5A and 5B, this having a front and rear portion in addition to distal portions, but this particular embodiment being made of all cloth. This alternate preferred embodiment is also used to illustrate the use of secondary attachment bands (50a) and (50b) which provide an additional means for cables (16a) and (16b) to be attached to shoulder harness member (12). The use of the secondary attachment bands allows the use of secondary cables (52a) and (52b) which typically join up with cables (16a) and (16b). The use of the additional cables and bands allows the force applied by tensioning means (18) to the patient's shoulders to be spread out over a greater area of the shoulders and upper torso.

Figure 6:
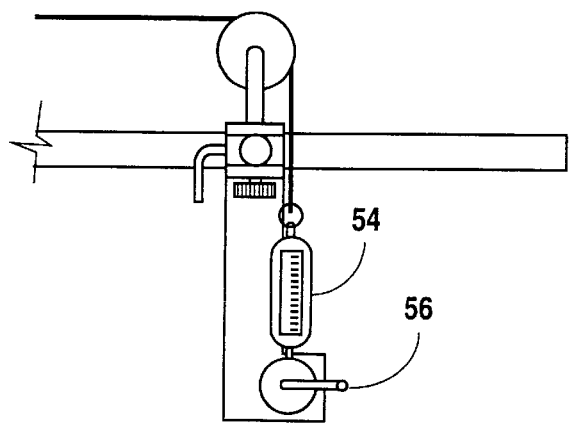
FIG. 6 is a side elevational view of an alternate preferred embodiment of a tensioning means of Applicant's present invention.

FIG. 6 illustrates an alternate preferred embodiment of tension means (18). In this embodiment, instead of the use of weights (28), a crank set stationary with respect to the table is attached to one end of a spring scale, the other end of the spring scale attached to the cable ends. By rotating the crank which is attached to the spring end of the scale, the amount of tension in the cables may be adjustably set, typically to balance one another. That is, if the first portion (20a) of tension means has 20 pounds of tension showing on the scale, second portion (20b) would typically be set at 20 pounds also.

Turning back to FIG. 1A for a moment, an alternate preferred embodiment might also be used which, instead of criss-crossing, cables (16a) and (16b) would have the cables run generally lateral to the edge of the table so that, for example, the cable coming from the right side of the shoulder harness would go down the right side of the table and the shoulder coming from the left side of the shoulder harness would run down the left side of the table, as viewed from above.

Figure 7:
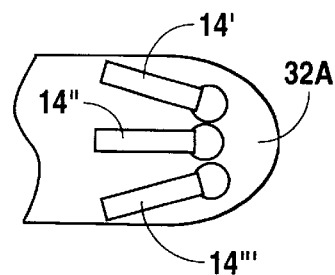
FIG. 7 is a top elevational view of the distal portion of the harness showing three different positions for attachment bands.

FIG. 7 illustrates that distal portions (32) of the body of the shoulder harness may contain include a multiplicity of attachment bands (14a'), (14a"), and (14'"), each typically having its own ring. This allows for positioning the patient either supine or prone on the examination table. The different angles of the straps with respect to the shoulder allows the user to either criss-cross the tensioning cables or run them straight down the table.

Terms such as "left," "right," "up," "down," "bottom," "top," "front," "back," "in," "out," and like are applicable to the embodiments shown and described in conjunction with the drawings. These terms are merely for purposes of description and do not necessarily apply to the position or manner in which the invention may be constructed for use.

Although the invention has been described in connection with the preferred embodiment, it is not intended to limit the invention's particular form set forth, but on the contrary, it is intended to cover such alternatives, modifications, and equivalences that may be included in the spirit and scope of the invention as defined by the appended claims.

What is claimed is:

1. A system for applying a force caudally to the shoulders of a patient laying flat on a hospital examination table, the device comprising:

a shoulder harness, including a body for engaging the upper torso of the patient, the body including a pair of distal portions, each distal portion laying adjacent the lateral aspect of each arm or shoulder of the patient, and each distal portion having an attachment band;

two cables, each having a first end and a second end;

means to applying tensional force to the first end of the two cables in a direction toward the feet of the patient;

means to engage the second end of each cable to the attachment bands of the shoulder harness.

2. The system of claim 1, wherein the shoulder harness includes a front portion and a back portion, the two portions including a neck opening.

3. The system of claim 2, wherein the neck opening includes an adjustable strap to increase or decrease the size thereof.

4. The system of claim 1, wherein means to apply tensional force includes weights attached to the first end of the cables and a pulley to allow the weight to hang from a frame member of the hospital examination table.

5. The system of claim 1 further including means to adjustably set the tension in the cables.

6. The system of claim 1, wherein means to apply a tensional force to the cables includes a spring scale, the spring scale being attached to the first end of the cable and further includes means to apply a force to the spring scale, which applied force will be transmitted through the spring scale to the cable to increase or decrease selectively the force applied to the shoulder harness.

7. The system of claim 1, wherein means to engage the second end of the straps to each of the shoulder bands of the harness includes a clip on the second end of the strap and a plastic loop on the attachment bands.

8. The system of claim 1, wherein means to engage the second end of the cable to each shoulder band includes a multiplicity of plastic loops at each shoulder strap of the harness.

9. The system of claim 1, wherein the attachment bands shoulder straps of the shoulder harness include a V-shaped yoke for enclosing a portion of the shoulder in the open end of the "V".

* * * * *